(12) United States Patent
Mori et al.

(10) Patent No.: US 10,167,495 B2
(45) Date of Patent: Jan. 1, 2019

(54) MICROBE QUANTIFYING APPARATUS AND MICROBE QUANTIFYING METHOD

(71) Applicant: HITACHI PLANT SERVICES CO., LTD., Tokyo (JP)

(72) Inventors: Shuichi Mori, Tokyo (JP); Noe Miyashita, Tokyo (JP); Yuta Nakatsuka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 159 days.

(21) Appl. No.: 14/435,878

(22) PCT Filed: Oct. 18, 2013

(86) PCT No.: PCT/JP2013/078334
§ 371 (c)(1),
(2) Date: Apr. 15, 2015

(87) PCT Pub. No.: WO2014/061786
PCT Pub. Date: Apr. 24, 2014

(65) Prior Publication Data
US 2015/0232909 A1    Aug. 20, 2015

(30) Foreign Application Priority Data

Oct. 19, 2012  (JP) .................. 2012-231766

(51) Int. Cl.
  *C12Q 1/06*    (2006.01)
  *G01N 21/64*   (2006.01)
(52) U.S. Cl.
  CPC ........... *C12Q 1/06* (2013.01); *G01N 21/6486* (2013.01)

(58) Field of Classification Search
  CPC .................. C12Q 1/06; G01N 21/6486
  See application file for complete search history.

(56) References Cited

U.S. PATENT DOCUMENTS

2004/0002126 A1\*  1/2004  Houde et al. ........ G01N 1/2205
                                                   435/7.32
2010/0216183 A1   8/2010  Okanojo et al.

FOREIGN PATENT DOCUMENTS

| JP | H08-023962 A | 1/1996 |
| JP | H11-137293 A | 5/1999 |
| JP | 2006-262821 A | 10/2006 |
| JP | 2010-193835 A | 9/2010 |
| WO | 2010/047779 A2 | 4/2010 |

OTHER PUBLICATIONS

May 7, 2014 Office Action issued in Japanese Patent Application No. 2012-231766.
Feb. 10, 2015 Office Action issued in Japanese Patent Application No. 2012-231766.
May 3, 2016 Extended European Search Report issued in European Patent Application No. 13847626.2.
(Continued)

*Primary Examiner* — Gautam Prakash
(74) *Attorney, Agent, or Firm* — Oliff PLC

(57) ABSTRACT

A microbe quantifying apparatus includes: a filtering mechanism that filters microbes contained in a fluid sample with a filter; a quantifying mechanism that quantifies the microbes with a specified biological material contained in the microbes on the filter as an index; and an anti-drying mechanism that prevents drying of the microbes on the filter.

2 Claims, 4 Drawing Sheets

(56) References Cited

OTHER PUBLICATIONS

Miyagi-Ken Nogyo; "Kogata luminometer ni yoru dojo biseibutsu biomass no shihyo to shite no ATP sokutei;" Fukyu ni Utsusu Gijutsu; Apr. 2011; No. 86, pp. 79 to 80.
Takuya Marumoto; "Dojo no biseibutsu biomass—hajimatta bakari no ryoteki haaku, sokutei gijutsu no hattatsu ni yori sono juyosei ga meikakuka;" Kagaku to Seibutsu; 1984; vol. 22; No. 12; pp. 824 to 826.
Sakae Inoue; "Saikin shinkin genchu kansensho shindan Kensa no tebiki;" 2009; pp. 1-32.

* cited by examiner

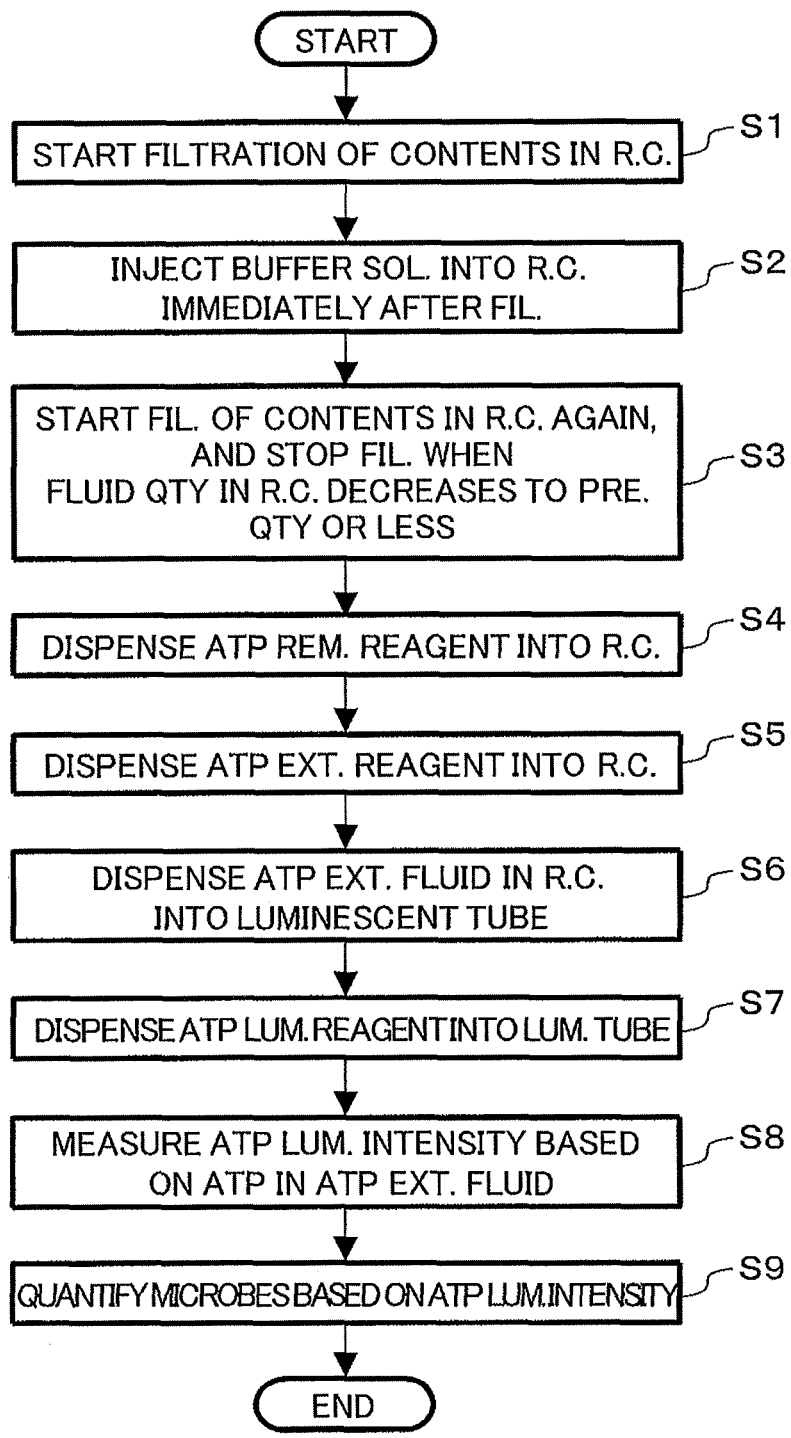

MICROBE QUANTIFYING APPARATUS AND MICROBE QUANTIFYING METHOD

TECHNICAL FIELD

The present invention relates to a microbe quantifying apparatus and a microbe quantifying method that filter microbes contained in a fluid sample with a filter and perform quantification of the microbes with a specified biological material contained in the microbes as an index.

BACKGROUND ART

As a quantifying method (counting method) for microbes contained in a specimen material, an ATP (adenosine triphosphate) method is conventionally known that quantifies ATP extracted from microbes to indirectly count the microbes.

Patent Literature 1 describes, in a method of detecting microbial count by ATP-bioluminescence method using a filtration membrane, completely removing noise luminescence points other than microbes to reliably determine presence or absence of one microbe.

This ATP method includes bringing an ATP extractive reagent into contact with trapped microbes to extract ATP inherent in the microbes and counting the microbes based on luminescence intensity obtained by reaction of a luminescent reagent to the ATP. This ATP method makes it possible to dramatically reduce the time required from the trapping of microbes until the counting thereof to one hour or about a few hours, while, for example, a culture method of counting microbes based on the number of colonies of microbes cultivated on a plate takes a few days.

Moreover, Patent Literature 2 describes a microbe quantifying method by which quantitative analysis of a large quantity of a fluid specimen can be performed rapidly and simply. This microbe quantifying method includes filtering the fluid specimen containing microbes with a filter and extracting ATP of the microbes allowed to remain on the filter.

CITATION LIST

Patent Literature

Patent Literature 1: Japanese Patent Application Publication No. H11-137293
Patent Literature 2: Japanese Patent Application Publication No. 2010-193835

SUMMARY OF INVENTION

Technical Problem

However, of the conventional microbe quantifying methods implemented in relation to the ATP method, the method including allowing the microbes in the fluid specimen to remain on the filter has posed a problem that sensitivity for measurement of the microbes is insufficient.

In view of this, an object of the present invention is to provide a microbe quantifying apparatus and a microbe quantifying method that quantify microbes in a fluid specimen with a biological material contained in the microbes as an index and have a better sensitivity for measurement of the microbes than ever before.

Solution to Problem

A microbe quantifying apparatus that solves the above problem includes a filtering mechanism that filters microbes contained in a fluid sample with a filter, a quantifying mechanism that quantifies the microbes with a specified biological material contained in the microbes on the filter as an index, and an anti-drying mechanism that prevents drying of the microbes on the filter.

Moreover, a microbe quantifying method that solves the above problem is a microbe quantifying method that filters microbes contained in a fluid sample with a filter and quantifies the microbes with a specified biological material contained in the microbes as an index, the microbe quantifying method including an anti-drying step of preventing drying of the microbes on the filter.

Advantageous Effects of Invention

The present invention can provide a microbe quantifying apparatus and a microbe quantifying method that quantify microbes in a fluid specimen with a biological material contained in the microbes as an index and have a better sensitivity for measurement of the microbes than ever before.

BRIEF DESCRIPTION OF DRAWINGS

FIG. 2 is a flowchart representing an outline of the microbe quantifying method according to the embodiment of the present invention.

DESCRIPTION OF EMBODIMENTS

Next, embodiments of the present invention will be described in detail with reference to the drawings as appropriate.

A microbe quantifying apparatus and a microbe quantifying method according to the present invention are mainly characterized by preventing drying of microbes which are objects to extract therefrom ATP (Adenosine TriPhosphate) as a biological material which is an index of quantification. Note that the definition of "drying of microbes" will be described in detail later.

In what follows, description will be given of the overall configuration of a microbe quantifying apparatus according to an embodiment of the present invention, and subsequently description will be given of the microbe quantifying method according to the present invention while description will be given of an operation of the microbe quantifying apparatus and the principle of quantification of microbes using the microbe quantifying apparatus.

<Overall Configuration of Microbe Quantifying Apparatus>

Figure 1:
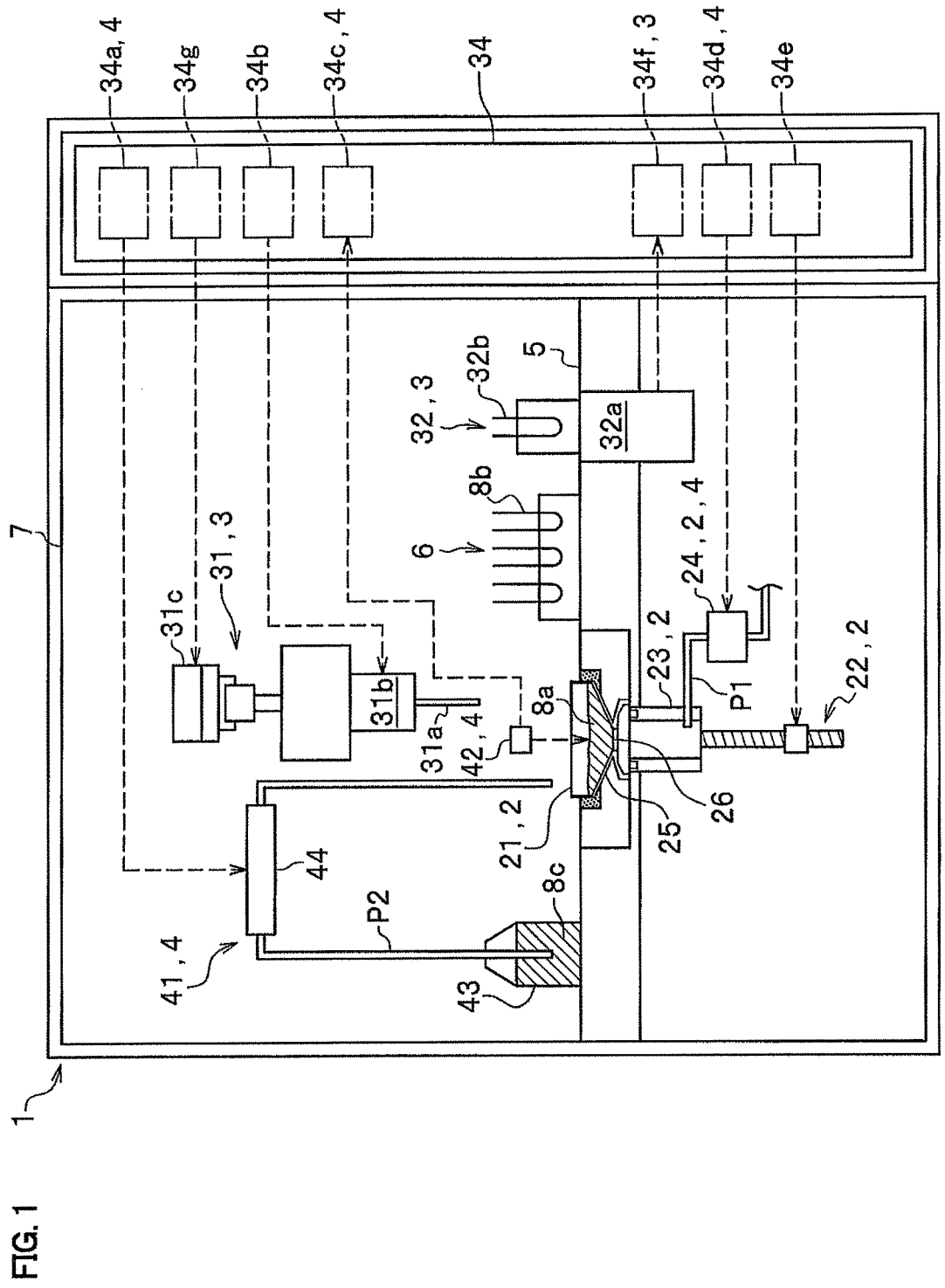
FIG. 1 is a diagram for explaining a configuration of a microbe quantifying apparatus according to an embodiment of the present invention.

As shown in FIG. 1, a microbe quantifying apparatus 1 is configured to be provided with a filtering mechanism 2 that filters microbes contained in a fluid sample 8a with a filter 26, a quantifying mechanism 3 that performs quantification of microbes with ATP (biological material) of the microbes obtained on the filter 26 as an index, and an anti-drying mechanism 4 that prevents drying of the microbes on the filter 26.

(Filtering Mechanism)

As shown in FIG. 1, the filtering mechanism 2 is provided with a recovery container 21 having the filter 26 inside thereof, a suction head 23, a lifting and lowering mechanism 22 that moves the suction head 23 up and down, and a suction pump 24 that sucks contents in the recovery container 21 by vacuuming through the suction head 23.

The recovery container 21 is adapted to isolate microbes contained in the fluid sample 8a fed thereinto and to extract ATP of the isolated microbes to recover it. Description will be given in detail later of a process of isolation of microbes from the fluid sample 8a and a process of extraction of ATP.

The recovery container 21 is configured with the filter 26 provided at the bottom portion of a funnel-shaped body 25. The filter 26 in the present embodiment has a two-ply composition of a hydrophilic filter 26a (see FIG. 3E) and a hydrophobic filter 26b (see FIG. 3E) as will be described later. Although not illustrated in FIG. 1, the hydrophilic filter 26a is disposed on the upper side of the two-ply composition and the hydrophobic filter 26b is disposed on the lower side of the two-ply composition.

The filter 26 thus configured is adapted to hold thereon the fluid sample 8a fed into the body 25 so long as suction is not performed through the suction head 23 to be next described. Also, when suction is performed through the suction head 23, the filter 26 is adapted to allow microbes (not shown) of the fluid sample 8a to remain on the filter 26, and to enable fluid constituents of the fluid sample 8a to be discharged through the filter 26 to the side of the suction head 23.

Incidentally, the recovery container 21 is removably attached to a predetermined position on a treatment stage 5 provided in the microbe quantifying apparatus 1.

The suction head 23 is adapted to be movable up and down by the lifting and lowering mechanism 22 as described above, and when filtering the contents in the recovery container 21 with the filter 26, the lifting and lowering mechanism 22 lifts the suction head 23 to couple the suction head 23 and the recovery container 21 together. Moreover, when the recovery container 21 is attached to the treatment stage 5 or detached from the treatment stage 5, the lifting and lowering mechanism 22 lowers the suction head 23 to uncouple the coupling of the suction head 23 with the recovery container 21.

Upon start-up of the suction pump 24 which is provided in the middle of a pipe P1 extending out of the suction head 23, as described above, fluid constituents in the recovery container 21 is discharged through the filter 26, the suction head 23 and the suction pump 24 into a waste storage tank (not shown) in the microbe quantifying apparatus 1.

(Quantifying Mechanism)

As shown in FIG. 1, the quantifying mechanism 3 is configured to be mainly provided with a fluid dispensing device 31, a luminescence intensity measuring unit 32, and a computing unit 34f of a control unit 34 that quantifies microbes based on a detection signal of ATP luminescence intensity which is output from the luminescence intensity measuring unit 32.

The fluid dispensing device 31 is provided with a fluid dispensing nozzle 31a, a dispensing pump 31b that allows the fluid dispensing nozzle 31a to suck or discharge a predetermined quantity of fluid, an actuator 31c that three-dimensionally moves the fluid dispensing nozzle 31a in a housing 7 of the microbe quantifying apparatus 1, and a second flow rate control unit 34b of the control unit 34.

The fluid dispensing nozzle 31a of the fluid dispensing device 31 dispenses predetermined quantity of ATP extraction fluid, which is obtained in the recovery container 21 in a process to be described later, into a luminescent tube 32b of the luminescence intensity measuring unit 32 to be next described. Also, the fluid dispensing nozzle 31a dispenses an ATP luminescent reagent 8b in a reagent holder 6 into the luminescent tube 32b.

Note that three-dimensional movement of the fluid dispensing nozzle 31a by the actuator 31c of the fluid dispensing device 31 is realized by predetermined control for the actuator 31c by an actuator control unit 34g of the control unit 34. Also, adjustment of the quantity to be dispensed such as the ATP extraction fluid and the ATP luminescent reagent 8b is realized by predetermined control for the dispensing pump 31b by the second flow rate control unit 34b.

The luminescence intensity measuring unit 32 is provided with the luminescent tube 32b into which the ATP extraction fluid and the ATP luminescent reagent 8b are dispensed to cause luminescent reaction, and a photodetector unit 32a having a photomultiplier tube that detects ATP luminescence intensity at the time of luminescent reaction.

The photodetector unit 32a outputs a detection signal of ATP luminescence intensity to the computing unit 34f of the control unit 34 as described above.

The computing unit 34f is configured to quantify microbes contained in the fluid sample 8a fed into the recovery container 21, based on the detection signal of ATP luminescence intensity output from the photodetector unit 32a. Steps for quantification of microbes by the computing unit 34f will be described in detail later.

(Anti-Drying Mechanism)

As shown in FIG. 1, the anti-drying mechanism 4 in the present embodiment is provided with a buffer solution injector 41 that injects buffer solution 8c into the recovery container 21, the suction pump 24 that is also the component of the filtering mechanism 2 described above, a level gauge 42 that detects fluid quantity in the recovery container 21 to output a fluid quantity detection signal. Also, the anti-drying mechanism 4 is configured to be provided with a fluid quantity detection signal inputting unit 34c, a suction pump control unit 34d and a first flow rate control unit 34a of the control unit 34.

The fluid quantity detection signal inputting unit 34c determines, based on a fluid quantity detection signal output from the level gauge 42, whether or not the fluid quantity in the recovery container 21 has decreased to a predetermined quantity or less. When the fluid quantity detection signal inputting unit 34c determines that the fluid quantity in the recovery container 21 has decreased to the predetermined quantity or less, the suction pump control unit 34d stops the suction pump 24 and the first flow rate control unit 34a starts up the buffer solution injector 41. Note that the buffer solution 8c corresponds to "replacement fluid" set forth in the claims and the buffer solution injector 41 corresponds to "fluid replacement mechanism" set forth in the claims.

The anti-drying mechanism 4 thus configured is adapted to prevent drying of the microbes on the filter 26 as described above. Also, "drying of microbes" in the present embodiment means enough drying to inhibit normal activity of the microbes. Accordingly, the state in which water films covering surfaces of cells of the microbes merely evaporate into the atmosphere does not mean the drying defined herein. Incidentally, when the microbes are dried, the quantity of extraction of ATP decreases because the reason is considered such as difficulty in resynthesis of ATP due to decrease in biological activity.

As shown in FIG. 1, the buffer solution injector 41 is provided with a buffer solution storage tank 43, a pipe P2 which extends out of the buffer solution storage tank 43 and a tip of which is located above the recovery container 21, and a fluid feed pump 44 which is provided in the middle of the pipe P2.

The level gauge 42 in the present embodiment is configured to detect a distance from the level gauge 42 to a fluid level of the contents in the recovery container 21 to indirectly detect fluid quantity of the contents in the recovery container 21. Note that the level gauge 42 corresponds to "fluid quantity detection unit" set forth in the claims. Although the level gauge 42 is not limited to a specific one, an optical level gauge using laser light or the like can be preferably used.

The fluid quantity detection signal inputting unit 34c of the control unit 34 is constituted by an interface, an A/D converter and the like, and is adapted to input the fluid quantity detection signal from the level gauge 42. Then, a central processing unit (not shown), a storing unit (not shown) and the like, which are included in the suction pump control unit 34d and the first flow rate control unit 34a, respectively, cooperate with one another based on the fluid quantity detection signal input via the fluid quantity detection signal inputting unit 34c, to allow the suction pump control unit 34d and the first flow rate control unit 34a to stop the suction pump 24 to be driven and start up the buffer solution injector 41 (fluid feed pump 44) as described above. Note that the suction pump control unit 34d and the first flow rate control unit 34a may employ the central processing unit (not shown), the storing unit (not shown) and the like which are common to each other, or the suction pump control unit 34d and the first flow rate control unit 34a may employ the central processing unit (not shown), the storing unit (not shown) and the like which are independently of each other.

<Operation of Microbe Quantifying Apparatus and Principle of Quantification of Microbes>

Next, description will be given of the microbe quantifying method according to the present invention while description will be given of an operation of the microbe quantifying apparatus 1 and the principle of quantification of microbes. Herein, description will be given with reference to FIG. 1 and FIG. 2. FIG. 2 is a flowchart representing an outline of the microbe quantifying method according to the embodiment of the present invention.

In the microbe quantifying apparatus 1 shown in FIG. 1, the recovery container 21 is first arranged on the treatment stage 5, the fluid sample 8a which is a test object is then injected into the recovery container 21, and subsequently, a start-up switch (not shown) is turned on to allow the control unit 34 to execute the following steps.

A lifting and lowering mechanism control unit 34e of the control unit 34 issues an instruction to the lifting and lowering mechanism 22 to lift the suction head 23 to be coupled with the recovery container 21.

Next, the suction pump control unit 34d of the control unit 34 starts up the suction pump 24 to allow the suction head 23 to start filtration of the contents (fluid sample 8a) in the recovery container 21 (step S1 in FIG. 2). By the filtration process of step S1, microbes are recovered on the filter 26 and fluid constituents of the fluid sample 8a are discharged to the side of the suction head 23. In doing so, most of ATPs which are contained in the fluid constituents of the fluid sample 8a and exist outside the cells of the microbes, and substances which inhibit ATP luminescent reaction to be described later, are also discharged together with the fluid constituents.

Next, immediately after the filtration of the contents in the recovery container 21 is completed, the buffer solution 8c is injected into the recovery container 21 (step S2 in FIG. 2). Herein, "immediately after the filtration" means that the time required from when the fluid constituents in the recovery container 21 completely run down through the filter 26 until starting to inject the buffer solution 8c is made as shorter as possible, and when possible, it is preferable to be within five minutes.

The process of step S2 causes the microbes recovered on the filter 26 to be prevented from drying. The process of step S2 corresponds to "anti-drying process" set forth in the claims.

Next, the suction pump control unit 34d of the control unit 34 starts up the suction pump 24 to allow the suction head 23 to start filtration of the contents in the recovery container 21 again (step S3 in FIG. 2). Also, the suction pump control unit 34d of the control unit 34 stops the filtration when the fluid quantity in the recovery container 21 decreases to the predetermined quantity or less, based on the fluid quantity detection signal from the level gauge 42 (step S3 in FIG. 2).

The process of step S3 also causes the microbes on the filter 26 to be prevented from drying. The process of step S3 also corresponds to "anti-drying process" set forth in the claims.

In the next step S4, ATP removal reagent is dispensed into the recovery container 21 (step S4 in FIG. 2). Incidentally, the ATP removal reagent is set in the reagent holder 6 and is dispensed by the fluid dispensing nozzle 31a of the fluid dispensing device 31 described above from the reagent holder 6 into the recovery container 21.

Dispensing the ATP removal reagent causes ATP existing outside the cells of the microbes to be more certainly removed.

Examples of the ATP removal reagent include ATP-degrading enzyme.

Also, the fluid dispensing nozzle 31a of the fluid dispensing device 31 dispenses an ATP extractive reagent into the recovery container 21 based on the predetermined controls for the actuator 31c and the dispensing pump 31b by the actuator control unit 34g and the second flow rate control unit 34b as described above (step S5 in FIG. 2).

Dispensing the ATP extractive reagent causes ATP contained in the microbes to be extracted to produce the ATP extraction fluid in the recovery container 21.

As examples of the ATP extractive reagent, surfactant, mixture of ethanol and ammonia, methanol, ethanol, trichloroacetic acid, perchloric acid, tris-buffered solution, and the like, can be preferably used. In particular, the surfactant is preferable to the others. Examples of the surfactant include sodium dodecyl sulfate, potassium lauryl sulfate, sodium monolauroyl phosphate, sodium alkylbenzene sulfonate, benzalkonium chloride, benzethonium chloride, cetylpyridinium chloride, cetyltrimethylammonium bromide, myristyldimethylbenzylammonium chloride, and the like.

Next, the fluid dispensing nozzle 31a of the fluid dispensing device 31 dispenses the ATP extraction fluid in the recovery container 21 into the luminescent tube 32b of the luminescence intensity measuring unit 32 based on the predetermined controls for the actuator 31c and the dispensing pump 31b by the actuator control unit 34g and the second flow rate control unit 34b as described above (step S6 in FIG. 2).

Moreover, the fluid dispensing nozzle 31a dispenses the ATP luminescent reagent 8b set in the reagent holder 6 into the luminescent tube 32b based on the predetermined controls for the actuator 31c and the dispensing pump 31b by the actuator control unit 34g and the second flow rate control unit 34b as described above (step S7 in FIG. 2).

Examples of the ATP luminescent reagent 8b include luciferase-luciferin reagent.

This causes luminescent reaction between the ATP contained in the ATP extraction fluid and the ATP luminescent reagent 8b in the luminescent tube 32b to produce luminescence.

Next, the computing unit 34f of the control unit 34 digitally processes a signal which is output based on detection of luminescence of ATP from the photodetector unit 32a (see FIG. 1), and measures luminescence intensity based on the single-photon counting method (step S8 in FIG. 2). Then, the control unit 34 computes the quantity of ATP (amol) contained in the ATP extraction fluid dispensed into the luminescent tube 32b, based on a calibration curve which is stored in advance in a storing unit (not shown) and represents the relationship between the quantities of ATP (amol) and luminescence intensities (CPS). The control unit 34 performs quantification of microbes as an ATP corresponding value of the microbe equivalent contained in the fluid sample 8a, based on the computed quantity of ATP (amol) (step S9 in FIG. 2). When this step S9 is carried out, the predetermined process of a sequence of microbe quantifying method according to the present embodiment comes to an end.

According to the microbe quantifying apparatus 1 and the microbe quantifying method of the present embodiment as described above, the following operation and effect can be exhibited. FIGS. 3A to 3D to be next referred to are cross-sectional views showing the recovery container and fluid levels in the recovery container when carrying out the above microbe quantifying method. FIGS. 3E to 3H are schematic views showing conditions near the filter in situations corresponding to FIGS. 3A to 3D, in an enlarged manner.

Note that in FIGS. 3E to 3H, the microbe indicated by reference sign B actually has the size of micrometers, and the ATP actually has a molecular size. FIGS. 3E to 3H do not reflect thereon the relative size between the microbe and the ATP.

Figure 3A:
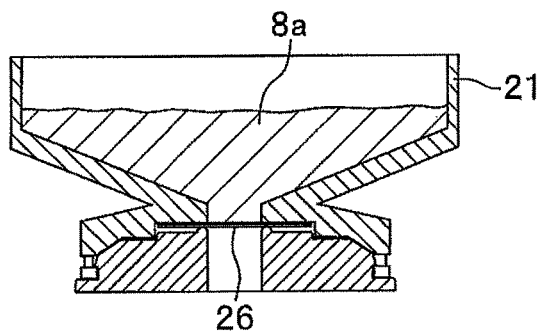
FIGS. 3A to 3D are cross-sectional views showing a recovery container and fluid levels in the recovery container when carrying out the microbe quantifying method according to the embodiment of the present invention.

In the above step S1 (see FIG. 2), just before filtration of the contents in the recovery container 21 is started, the recovery container 21 is filled with a predetermined quantity (10 ml in the present embodiment, but not limited to this) of fluid sample 8a as shown in FIG. 3A. Note that in FIG. 3A, reference sign 26 denotes the filter.

Figure 3E:
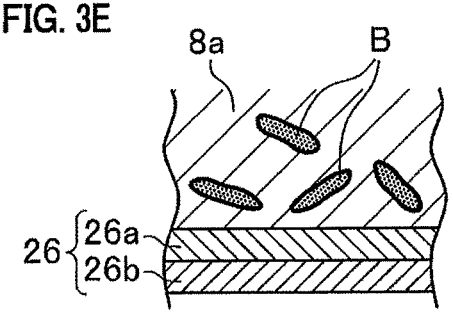
FIGS. 3E to 3H are schematic views showing conditions near a filter in situations corresponding to FIGS. 3A to 3D, in an enlarged manner.

Also, as shown in FIG. 3E, the fluid sample 8a filled on the filter 26 contains the microbes B. Note that in FIG. 3E, reference sign 26a denotes the hydrophilic filter as described above, and reference sign 26b denotes the hydrophobic filter as described above.

Figure 3B:
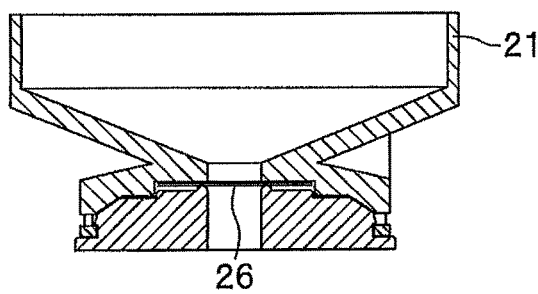
Figure 3F:
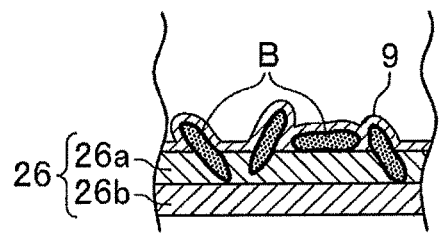

When the filtration in step S1 (see FIG. 2) is finished, the recovery container 21 is brought into a visually empty state as shown in FIG. 3B. Also, as shown in FIG. 3F, the microbes B are allowed to remain on the filter 26 (26a, 26b). More specifically, the microbes B are allowed to remain on the filter 26 with a water film 9 microscopically formed on the surfaces of the microbes B just after the filtration.

In step S2 (see FIG. 2), when the buffer solution 8c is injected into the recovery container 21 immediately after the filtration, the recovery container 21 is filled with the buffer solution 8c, although not shown, with nearly the same quantity as in FIG. 3A.

Figure 3C:
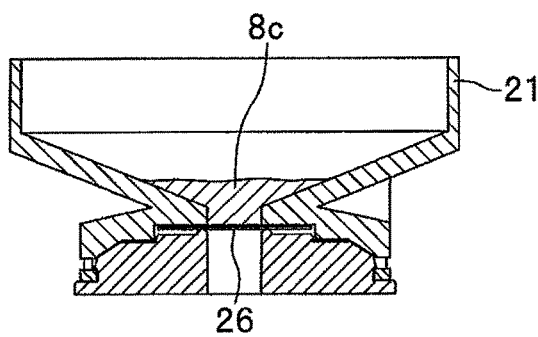
Figure 3G:
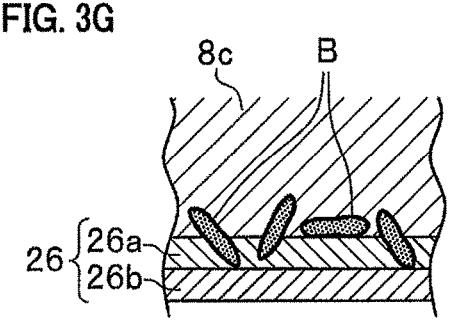

In step S3 (see FIG. 2), when filtration is started again and subsequently the fluid quantity in the recovery container 21 decreases to the predetermined quantity or less to stop the filtration, a small quantity of buffer solution 8c remains on the filter 26 in the recovery container 21 as shown in FIG. 3C. Incidentally, the remaining quantity of the buffer solution 8c in the present embodiment is 0.1 ml, but not limited to this. Consequently, the microbes B are brought into a state immersed in the buffer solution 8c on the filter 26 as shown in FIG. 3G.

Figure 3D:
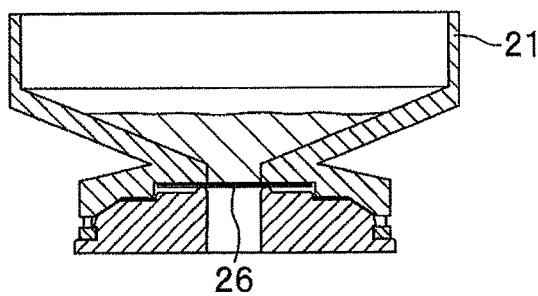

Then, when the ATP removal reagent is dispensed into the recovery container 21 in step S4 (see FIG. 2) and the ATP extractive reagent is dispensed into the recovery container 21 in step S5 (see FIG. 2), the fluid quantity in the recovery container 21 increases as shown in FIG. 3D, more than the fluid quantity shown in FIG. 3C, depending on the dispensing quantities of the ATP removal reagent and the ATP extractive reagent.

Incidentally, the dispensing quantities of the ATP removal reagent and the ATP extractive reagent are actually small and thus, for convenience of drawing figures, the increase in fluid quantity shown in FIG. 3C and FIG. 3D is overdrawn.

Figure 3H:
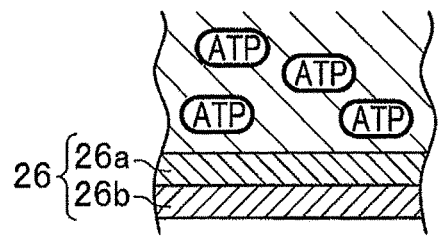

Also, as shown in FIG. 3H, the ATP extraction fluid including ATP contained in the buffer solution is produced in the recovery container 21. Incidentally, the ATP removal reagent which is an enzyme system is deactivated upon contact with the ATP extractive reagent which is a surfactant system. Thus the ATP removal reagent employed in step S4 hardly has effect on the measurement of ATP luminescence intensity in step S8 (see FIG. 2).

According to the microbe quantifying apparatus 1 and the microbe quantifying method of the present embodiment as described above, injection of the buffer solution 8c into the recovery container 21 (fluid replacement) is performed immediately after the filtration with the filter 26 (step S2 in FIG. 2), and thus drying of the microbes B allowed to remain on the filter 26 can be prevented.

Also, according to the microbe quantifying apparatus 1 and the microbe quantifying method of the present embodiment, the filtration is stopped when the fluid quantity in the recovery container 21 decreases to the predetermined quantity or less (step S3 in FIG. 2), and thus drying of the microbes B on the filter 26 can be prevented.

Moreover, according to the microbe quantifying apparatus 1 and the microbe quantifying method thus configured, drying of the microbes B can be prevented and thus yield of ATP obtained from the microbes B contained in the fluid sample 8a is even more improved than ever before. This allows the microbe quantifying apparatus 1 and the microbe quantifying method to have a better sensitivity for measurement (sensitivity for quantification) of the microbes B than ever before.

Note that it is assumed to be due to the fact that drying of the microbes B is prevented to maintain biological activity of the microbes B (viable bacteria) to thereby suppress a decrease in the declining rate of ATP in the microbes B (viable bacteria), that the microbe quantifying apparatus 1 and the microbe quantifying method of the present embodiment allow the yield of ATP obtained from the microbes B to be more improved than ever before.

Although the embodiment of the present invention has been described as above, the present invention is not limited to the above embodiment and can be carried out in a variety of forms.

Although the above embodiment has adopted the configuration in which drying of the microbes B is prevented by performing injection of the buffer solution 8c into the recovery container 21 immediately after the filtration, or by stopping the filtration when the fluid quantity in the recovery container 21 decreases to the predetermined quantity or less, the present invention is not limited to the embodiment as long as it includes the process of preventing drying of the microbes B.

Figure 4:
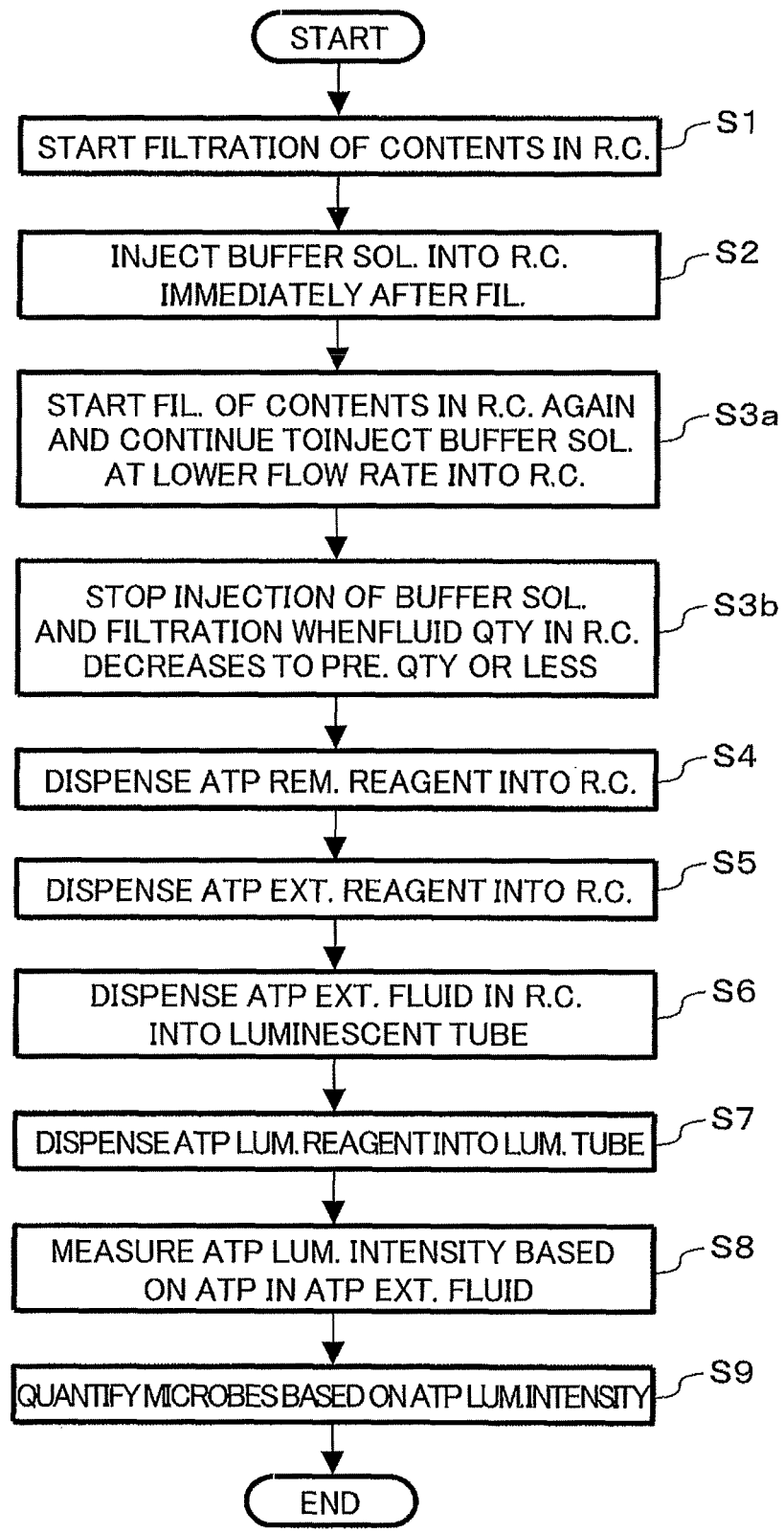
FIG. 4 is a flowchart representing an outline of the microbe quantifying method according to another embodiment of the present invention.

FIG. 4 is a flowchart representing an outline of the microbe quantifying method which is carried out by the microbe quantifying apparatus 1, as another embodiment (modified example) of the present invention. The microbe quantifying method shown in FIG. 4 is the same as the microbe quantifying method shown in FIG. 2 except that step S3 in FIG. 2 is replaced with steps S3a and S3b in FIG. 4, as compared to the microbe quantifying method shown in FIG. 2. Thus, in this modified example, description of steps S1, S2 and S4 to S9 will be omitted and description will be given of only steps S3a and S3b.

As shown in FIG. 4, the microbe quantifying method includes, in step S3a after execution of step S2 thereof, starting filtration of the contents in the recovery container 21 again and continuing to inject the buffer solution 8c into the recovery container 21, at a lower flow rate than the flow rate of the buffer solution 8c in step S2. Thus the filtration is continued while the buffer solution 8c is being added into the recovery container 21, thereby allowing the fluid quantity in the recovery container 21 to gradually decrease. This causes ATP existing outside the cells to be removed effectively.

Then, in step S3b, the control unit 34 stops the injection of the buffer solution 8c and stops the filtration when the fluid quantity in the recovery container 21 decreases to the predetermined quantity or less. So, the fluid quantity in the recovery container 21 becomes the same as in FIG. 3C.

Consequently, according to this modified example, drying of the microbes B can be prevented and thus yield of ATP obtained from the microbes B contained in the fluid sample 8a is even more improved than ever before.

Also, although in the above embodiment, the ATP luminescent reagent 8b is dispensed into the luminescent tube 32b into which the ATP extraction fluid has been dispensed, to cause luminescent reaction, the present invention can also adopt a configuration in which the ATP extraction fluid is dispensed into the luminescent tube 32b into which the ATP luminescent reagent 8b has been dispensed, to cause luminescent reaction.

Examples of the microbes B in the above embodiment include, but are not limited to, Gram-positive bacteria such as *Corynebacterium, Micrococcus, Staphylococcus aureus, Staphylococcus epidermidis, Bacillus cereus* or *Bacillus subtilis*, Gram-negative bacteria such as *Citrobacter, Bacillus coli, Pseudomonas aeruginosa* or *serratia* bacteria, true fungus such as *Aspergillus, Penicillium, Wallemia sebi* or *Candida*, and the like.

Note that, in the case of applying the present invention to spore forming bacteria such as *Bacillus subtilis*, the reagent described above can include trophozoite cell conversion reagent such as amino acid, sugar or the like.

Also, although in the above embodiment, quantification of the microbes B is performed using the ATP method, the present invention can also perform quantification of the microbes B based on fluorescence which is caused by irradiating biological material such as DNA, RNA or NAD extracted from the microbes B with an excitation light.

Moreover, in the case of quantifying Gram-negative bacteria, the quantification can also be performed with endotoxin contained in the cell membrane as an index and based on luminescence intensity obtained by reaction of limulus to the endotoxin.

Furthermore, although in the above embodiment, quantification of the microbes B contained in the fluid sample 8a is assumed, for example, microbes suspended in the air may be trapped on a gel-like carrier and subsequently the buffer solution 8c and the like may be added with the gel-like carrier disposed in the recovery container 21 to form the fluid sample 8a.

Incidentally, examples of the gel-like carrier include what is formed of a material that changes in phase from gel to sol by the change from ordinary temperature to elevated temperature. As the material, it is preferable to use what liquefies at 30 degrees Celsius or more and at less than 40 degrees Celsius, and it is more preferable to use gelatin, a mixture of gelatin and glycerol, or a copolymer with a ratio of 10:1 of N-acryloyl glycine amide and N-methacryloyl-N'-biotinyl propylene diamine.

REFERENCE SIGNS LIST

1 Microbe quantifying apparatus
2 Filtering mechanism
3 Quantifying mechanism
4 Anti-drying mechanism
6 Reagent holder
8a Fluid sample
8b ATP luminescent reagent
8c Buffer solution
21 Recovery container
22 Lifting and lowering mechanism
23 Suction head
24 Suction pump
26 Filter
26a Hydrophilic filter
26b Hydrophobic filter
31 Fluid dispensing device
31a Fluid dispensing nozzle
31b Dispensing pump
31c Actuator
32 Luminescence intensity measuring unit
32a Photodetector unit
32b Luminescent tube
34 Control unit
34a First flow rate control unit
34b Second flow rate control unit
34c Fluid quantity detection signal inputting unit
34d Suction pump control unit
34e Lifting and lowering mechanism control unit
34f Computing unit
34g Actuator control unit
41 Buffer solution injector
42 Level gauge
43 Buffer solution storage tank
44 Fluid feed pump
B microbe

The invention claimed is:

1. A microbe quantifying apparatus comprising:
a filtering mechanism that is configured to filter microbes contained in a fluid sample with a filter having an upper layer of a hydrophilic filter and a lower layer of a hydrophobic filter;
a quantifying mechanism that is configured to quantify the microbes with a specified biological material contained in the microbes on the filter as an index; and an anti-drying mechanism that is configured to prevent drying of the microbes on the filter, wherein the anti-drying mechanism includes:

a level gauge that is configured to detect fluid quantity on the filter to output a fluid quantity detection signal, a buffer solution injector that is configured to supply buffer solution fluid onto the filter, and a control unit that is configured to:

perform a filtration control based on the fluid quantity detection signal, wherein the control unit is configured to: (i) activate the buffer solution injector to supply buffer solution onto the filter when determining based on the fluid quantity detection signal that the fluid quantity has decreased to a predetermined quantity or less, and (ii) stop the filtering mechanism when the fluid quantity on the filter decreases to the predetermined quantity or less, based on the fluid quantity detection signal from the level gauge, and perform a control to couple and decouple the suction head to the filtering mechanism.

2. The microbe quantifying apparatus according to claim 1, wherein the control to couple and decouple the suction head comprises a lifting and lowering, respectively, of the suction head.

\* \* \* \* \*